United States Patent [19]

Yamada et al.

[11] Patent Number: 4,855,298

[45] Date of Patent: * Aug. 8, 1989

[54] 6-HALO-1,2,3,4-TETRAHYDROQUINAZO-LINE-4-SPIRO-4-IMIDAZOLIDINE-2,2'5'-TRIONES USEFUL FOR THE TREATMENT AND PROPHYLAXIS OF DIABETIC COMPLICATIONS

[75] Inventors: Yoshihisa Yamada, Kyoto; Yuzo Matsuoka, Toyonaka, both of Japan

[73] Assignee: Tanabe Seiyaku Co., Ltd., Japan

[ * ] Notice: The portion of the term of this patent subsequent to Aug. 9, 2005 has been disclaimed.

[21] Appl. No.: 114,569

[22] Filed: Oct. 29, 1987

[30] Foreign Application Priority Data

Nov. 21, 1986 [JP] Japan .................... 61-279421

[51] Int. Cl.⁴ .................. A61K 31/505; C07D 487/10
[52] U.S. Cl. .................... 514/259; 544/231; 548/485; 560/30
[58] Field of Search ............ 514/259; 544/230, 231, 544/286

[56] References Cited

U.S. PATENT DOCUMENTS

| | | | |
|---|---|---|---|
| 4,248,882 | 2/1981 | Sarges | 546/18 |
| 4,273,775 | 6/1981 | Sarges | 546/18 |
| 4,282,229 | 8/1981 | Sarsas | 514/278 |
| 4,533,667 | 8/1985 | Hutchison | 514/278 |
| 4,575,507 | 3/1986 | Lipinski | 514/278 |
| 4,762,839 | 8/1988 | Yamada et al. | 514/259 |

FOREIGN PATENT DOCUMENTS

| | | |
|---|---|---|
| 321911 | 4/1975 | Austria . |
| 28906 | 5/1981 | European Pat. Off. . |
| 101149 | 2/1984 | European Pat. Off. . |
| 127412 | 12/1984 | European Pat. Off. . |
| 138490 | 4/1985 | European Pat. Off. . |
| 191735 | 8/1986 | European Pat. Off. . |
| 204534 | 12/1986 | European Pat. Off. . |
| 3128606 | 5/1982 | Fed. Rep. of Germany . |
| 53-653 | 5/1978 | Japan . |
| 95582 | 7/1979 | Japan . |
| 104876 | 8/1981 | Japan . |
| 45185 | 3/1982 | Japan . |

OTHER PUBLICATIONS

Capuano et al., I, *Chem. Ber.*, 103, p. 2394 (1970).
Capuano et al., II, *Chem. Ber.*, 110, p. 3849 (1977).

*Primary Examiner*—Anton H. Sutto
*Assistant Examiner*—Emily Bernhardt
*Attorney, Agent, or Firm*—Scully, Scott, Murphy & Presser

[57] ABSTRACT

A quinazolinone derivative of the formula:

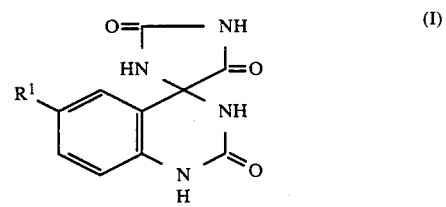

wherein $R^1$ is hydrogen atom or a halogen atom, or a salt thereof and processes for preparing the same are disclosed. The quinazolinone derivative (I) is useful for treatment of diabetic complications.

7 Claims, No Drawings

6-HALO-1,2,3,4-TETRAHYDROQUINAZOLINE-4-SPIRO-4-IMIDAZOLIDINE-2,2′,5′-TRIONES USEFUL FOR THE TREATMENT AND PROPHYLAXIS OF DIABETIC COMPLICATIONS

This invention relates to a novel quinazolinone derivative and processes for preparing the same. More particularly, it relates to a novel quinazolinone derivative of the formula:

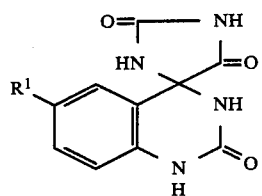
(I)

wherein $R^1$ is hydrogen atom or a halogen atom, or a salt thereof.

It is known that diabetic complications include diabetic neurosis, diabetic, cataract, diabetic microangiopathy such as diabetic retiopathy, and diabetic nephrosis, and the like. These diabetic complications are induced by accumulation of polyols such as sorbitol which are produced in vivo from hexose by aldose reductase [cf. The New England Journal of Medicine, Vol. 288, 831–836 (1973)]. In order to prevent and treat the diabetic complications, there have been proposed various aldose reductase inhibitors which can inhibit the accumulation of polyols within the body, for instance, compounds having chroman nucleus (cf. Japanese Patent Publication (unexamined) Nos. 53653/1978 and 45185/1982, and U.S. Pat. No. 4,117,230), compounds having thiazolidine nucleus (cf. Japanese Patent Publication (unexamined) No. 104876/1981), and compounds having phthalazine nucleus (cf. Japanese Patent Publication (unexamined) No. 95582/1979).

On the other hand, Chemie Berichte, Vol. 103, 2394 (1970) and ibid. Vol. 110, 3849 (1977) disclose quinazolinone compounds such as 3,1′-dimethyl-1,2,3,4-tetrahydroquinazoline4-spiro-4′-imidazolidine-2,2′,5′-trione and 3,1′,3′-trimethyl-1,2,3,4-tetrahydroquinazoline-4-spiro-4′-imidazolidine-2,2′,5′-trione, but there has never been known any pharmacological activity of these quinazolinone compounds.

As a result of various investigations, we have now found that the compound (I) of the present invention or a salt thereof has excellent aldose reductase inhibitory activity and is useful for treatment of diabetic complications.

Representative examples of the compound of the present invention include those of the formula (I) in which $R_1$ is hydrogen or a halogen atom such as fluorine, chlorine or bromine. Preferred subgenus is those of the formula (I) in which $R^1$ is chlorine.

While the compound (I) of the present invention can exist in the form of two optical isomers due to one asymmetric carbon atom involved therein, all of these optical isomers or a mixture thereof are included within the scope of the invention.

According to the present invention, the compound (I) can be prepared, for example, by reacting a compound of the formula:

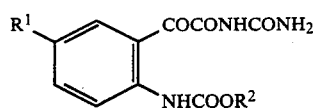
(II)

wherein $R^2$ is a lower alkyl and $R^1$ is the same as defined above, with ammonia or an ammonia doner.

Alternatively, the compound (I) in which $R^1$ is a halogen atom, i.e., a compound of the formula: wherein $R^{11}$ is a halogen atom, can be prepared by reacting a compound of the formula:

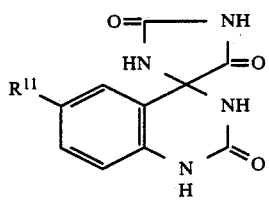
(I-a)

wherein $R^{11}$ is a halogen atom, can be prepared by reacting a compound of the formula:

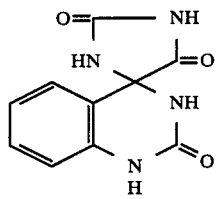
(I-b)

or a salt thereof, with a halogenating agent.

The reaction of the compound (II) with ammonia or the ammonia doner can be accomplished in a solvent. Examples of the compound (II) include those of the formula (II) in which $R^2$ is a lower alkyl such as methyl, ethyl, propyl or butyl. Any compound which releases ammonia in the reaction system can be used as the ammonia doner. Such ammonia doner includes, for example, ammonium salts such as ammonium acetate, ammonium formate or ammonium carbonate. Dichlorobenzene, toluene, methanol, ethanol, tetrahydrofuran or a mixture thereof is preferably used as the solvent. It is preferred to carry out the reaction at a temperature of room temperature to 200° C., preferably 50° to 160° C. When the reaction is carried out under mild reaction conditions, an intermediate product may be obtained as crystals. The intermediate product is further reacted with ammonia or the ammonia doner to give the compound (I).

The reaction of the compound (I-b) or a salt thereof with the halogenating agent can be accomplished in a solvent. Examples of the salt of the compound (I-b) include alkali metal salts such as sodium or potassium salt. Examples of the halogenating agent include sulfuryl chloride, chlorine, bromine, iodobenzene dichloride, N-bromosuccinimide, and the like. Acetic acid, tetrahydrofuran, dioxane, water or a mixture thereof is preferably used as the solvent. It is preferred to carry out the reaction at a temperature of 0° to 100° C., preferably 20° to 70° C.

When the compound (I) is obtained in the form of a racemic mixture, it may be resolved into each optical isomer by a conventional manner. For example, the optical resolution may be carried out by reacting the racemic mixture of the compound (I) with a resolving agent in a solvent, isolating the crystals of a less soluble diastereoisomeric salt by utilizing the difference in solubility of two diastereoisomeric salts and further isolating the more soluble diastereoisomeric salt from the mother liquor. The diastereoisomeric salts thus obtained can be converted to the desired optically active compound (I), for example, by treating with an acid.

The starting compound (II) used in the present invention is also novel and can be prepared, for example, by reacting a compound of the formula:

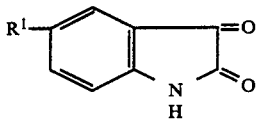

(III)

wherein $R^1$ is the same as defined above, or a salt thereof with a compound of the formula:

$R^2OCOX$ (IV)

wherein X is a hologen atom and $R^2$ is the same as defined above, in the presence of a base (e.g., triethylamine etc.) at a temperature of 0° to 80° C. in a solvent to give a compound of the formula:

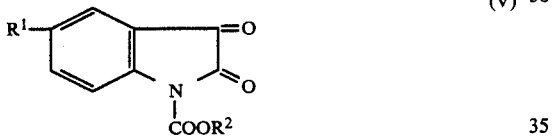

(V)

wherein R1 and $R^2$ are the same as defined above, and reacting the compound (V) with urea at a temperature of 50° to 120° C. in a solvent.

The compound (I) of the present invention can be used as a medicament either in the free form or in the form of a pharmaceutically acceptable salt thereof. The pharmaceutically acceptable salt includes, for example, sodium salt, potassium salt, calcium salt, lysine salt, ethylenediamine salt, diethanolamine salt, and the like. These salts can easily be prepared by treating the compound (I) with the corresponding base according to a conventional method.

As mentioned hereinbefore, the compound (I) and its salt have excellent aldose reductase inhibitory activity and are useful for the treatment and/or prophylaxis of diabetic complications in warm-blooded animal, for example, diabetic neurosis, diabetic cataract, and diabetic microangiopathy such as diabetic retinopathy and diabetic nephrosis.

The compound (I) and its salt of the present invention may be administered orally or parenterally, and may also be administered in the form of a pharmaceutical preparation containing the same compound in admixture with pharmaceutical excipients suitable for oral or parenteral administration. The pharmaceutical preparations include, for example, tablets, granules, powders, cupsules, injections, eye drugs (e.g., eyewash, eye ointement, etc.).

The dose of the compound (I) and pharmaceutically acceptable salts thereof may vary depending on the administration routes, the ages, weight and states of patients, severity of diseases, and the like, but is usually in the range of about 0.01 to 200 mg/kg/day, preferably 0.1 to 50 mg/kg/day.

EXPERIMENT

Inhibitory activity against accumulation of polyols:
(Method)

Slc:Wistar male rats (3–4 weeks old, one group: 3 rats) were fed with (i) a 20% galactose-added diet containing 20 mg % of a test compound (i.e., the test compound being contained in an amount of 20 mg per 100 g of the diet) (test compound-administered group), (ii) a 20% galactose-added diet (galactose control group), and (iii) a normal diet (no galactose) (normal control group) for 6 days. After the feeding, the rats were killed by cutting the carotid artery under ether anethesia, and immediately, the sciatic nerves at both sides were taken out, and the amount of polyols accumulated in the sciatic nerves was measured by the acetyl-acetone method described in Science, Vol. 182, 1146–1148 (1973). The polyol accumulation inhibition rate was calculated by the following equation.

Polyol accumulation inhibition rate (%) =

$$\left[1 - \frac{\left[\begin{array}{c}\text{Polyol amount (average) in test cmpd.-administd. group}\end{array}\right] - \left[\begin{array}{c}\text{Polyol amount (average) in normal control group}\end{array}\right]}{\left[\begin{array}{c}\text{Polyol amount (average) in galactose control group}\end{array}\right] - \left[\begin{array}{c}\text{Polyol amount (average) in normal control group}\end{array}\right]}\right] \times 100$$

(Results)

The results are shown in the following Table 1.

| Compound Nos. | Chemical name |
|---|---|
| | (The compound of the present invention) |
| 1 | 6-chloro-1,2,3,4-tetrahydroquinazoline-4-spiro-4'-imidazolidine-2,2',5'-trione |
| | (Known compounds) |
| 2 | 3,1'-dimethyl-1,2,3,4-tetrahydroquinazoline-4-spiro-4'-imidazolidine-2,2',5'-trione (disclosed in Chem. Ber., 103, 2394 (1970)) |
| 3 | 3,1',3'-trimethyl-1,2,3,4-tetrahydroquinazoline-4-spiro-4'-imidazolidine-2,2',5'-trione (disclosed in Chem. Ber., 110, 3849 (1977)) |

TABLE 1

| Compound Nos. | Polyol accumulation inhibition rate (%) |
|---|---|
| (The compound of the present invention) | |
| 1 | 83.7 |
| (Known compounds) | |
| 2 | 7.3 |
| 3 | 10.4 |

EXAMPLE 1

(1) Ethoxycarbonyl chloride (10.5 ml) is added dropwise to a mixture of 5-chloroisatin (18.16 g), tetrahydrofuran (180 ml) and triethylamine (15.3 ml) with stirring, and the mixture is stirred at room temperature for 5 minutes. The mixture is concentrated under reduced pressure to remove solvent, and water is added to the residue. Crystalline precipitates are collected by filtration, washed with isopropanol and isopropyl ether and then dried, whereby 5-chloro-1-ethoxycarbonylisatin (23.3 g) is obtained.

m.p. 169°–172° C. (decomp.).

(2) A mixture of 5-chloro-1-ethoxycarbonylisatin (15.2 g), tetrahydrofuran (150 ml) and urea (5.4 g) is refluxed for 18 hours, and the mixture is concentrated under reduced pressure to remove solvent. The residue is extracted with ethyl acetate, and the extract is concentrated under reduced pressure to remove solvent. The residue is chromatographed on silica gel (solvent, chloroform : methanol =9 : 1), and the fractions containing the desired compound are collected and concentrated under reduced pressure to remove solvent. Chloroform is added to the residue, and crystalline precipitates are collected by filtration and dried, whereby (5-chloro-2-ethoxycarbonylaminophenyl)oxalylurea (16.74 g) is obtained.

m.p. 189°–190° C. (decomp.).

(3) (5-Chloro-2-ethoxycarbonylaminophenyl)oxalylurea (6.27 g) is dissolved in a mixture of toluene (150 ml) and ethanol (15 ml), and 10% ammonia-ethanol solution (13.6 g) is added thereto. The mixture is stirred at 120° C. for 4 hours in a pressure bottle. After cooling, crystalline precipitates are collected by filtration, washed with toluene, ethanol and water, respectively, and then dried, whereby 6-chloro-1,2,3,4-tetrahydroquinazoline-4-spiro-4'-imidazolidine-2,2',5'-trione (3.46 g, yield: 64.9%) is obtained.

m.p. >280° C.

IR$\nu$ nujol/max (cm$^{-1}$): 3260, 3130, 1782, 1730, 1670, 1605.

MS(m/e): 268(M$^+$+1), 266(M$^+$−1).

NMR (DMSO-d$_6$)δ: 6.76(1H, d, J=9 Hz), 6.91(1H, d, J=3 Hz), 7.20(1H, d,d, J=9 Hz, J=3 Hz), 7.2(1H, br.s), 8.83(1H, s), 9.64(1H, s), 10.80(1H,s).

EXAMPLE 2

(1) Isatin (29.4 g) is treated in the same manner as described in Example 1-(1), whereby 1-ethoxycarbonylisatin (39.4 g) is obtained.

m.p. 113°–116° C. (decomp.).

(2) 1-Ethoxycarbonylisatin (2.79 g) is treated in the same manner as described in Example 1-(2), whereby (2-ethoxycarbonylaminophenyl)oxalylurea (2.42 g) is obtained.

m.p. 169°–170° C.

(3) (2-Ethoxycarbonylaminophenyl)oxalylurea (5.59 g) is treated in the same manner as described in Example 1-(3), whereby 1,2,3,4-tetrahydroquinazoline-4-spiro-4'-imidazolidine-2,2',5'-trione 2.74 g, yield: 53.2%) is obtained.

m.p. >280° C.

IR$\nu$ numol/max (cm$^{-1}$): 3260, 3150, 1782, 1729, 1670, 1606.

MS (m/e): 232(M+).

NMR (DMSO-d$_6$)δ: 6.6(4H, m), 7.84(1H, s), 8.79(1H, s), 9.49(1H, s), 10.73(1H, s).

EXAMPLE 3

(1) 5-Fluoroisatin (16.51 g) is suspended in tetrahydrofuran (170 ml), and triethylamine (14 ml) and ethoxycarbonyl chloride (9.5 ml) are added thereto under ice-cooling. The mixture is stirred for 10 minutes, and urea (9.0 g) is added thereto. The mixture is refluxed for 22 hours. After cooling, the mixture is concentrated under reduced pressure to remove solvent. Water is added to the residue, and the aqueous mixture is extracted with ethyl acetate. The extract is dried and concentrated under reduced pressure to dryness. The residue is chromatographed on silica gel (solvent, chloroform : methanol=10:1), and the fractions containing the desired compound are collected and concentrated under reduced pressure to remove solvent. The residue is crystallized with chloroform, and the crystals are collected by filtration, whereby (2-ethoxycarbonylamino-5-fluorophenyl)oxalylurea (10.77 g) is obtained.

m.p. 173°–176° C. (decomp.)

(2) (2-Ethoxycarbonylamino-5-fluorophenyl)oxalylurea (5.95 g) is treated in the same manner as described in Example 1-(3), whereby 6-fluoro-1,2,3,4-tetrahydroquinazoline-4-spiro-4'-imidazolidine-2,2',5'-trione (2.36 g) is obtained.

m.p. >280° C.

IR$\nu$ nujol/max (cm$^{-1}$): 3280, 3150, 1790, 1737, 1669, 1630, 1618.

NMR (DMSO-d$_6$)δ: 6.5–7.2(3H, m), 7.84(1H, s), 8.79(1H, s), 9.50(1H, s), 10.77(1H, s).

EXAMPLE 4

1,2,3,4-Tetrahydroquinazoline-4-spiro-4'-imidazolidine-2,2',5'-trione (1.16 g) is dissolved in acetic acid (800 ml) with heating. After cooling, sulfuryl chloride (0.75 g) is added to the mixture, and the mixture is stirred at room temperature for one hour and further stirred at 50° C. for one hour. The mixture is concentrated under reduced pressure to dryness, and crystalline residue thus obtained is collected by filtration, whereby 6-chloro-1,2,3,4-tetrahydroquinazoline-4-spiro-4'-imidazolidine-2,2',5'-trione (1.1 g) is obtained.

The physico-chemical properties of this product are identical with those of the product obtained in Example 1-(3).

What is claimed is:

1. A quinazolinone compound of the formula:

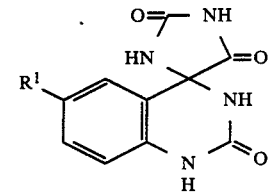

wherein R$^1$ is a halogen atom, or a non-toxic pharmaceutically acceptable salt thereof.

2. The compound claimed in claim 1 which is 6-chloro-1,2,3,4-tetrahydroquinazoline-4-spiro-4'-imidazolidine-2,2',5'-trione or a non-toxic pharmaceutically acceptable salt thereof.

3. The compound according to claim 1 in which halo is fluoro, chloro, or bromo.

4. A pharmaceutical composition which comprises a therapeutically effective amount of the compound according to claim 1 and a pharmaceutically acceptable carrier therefor.

5. The composition according to claim 4 in which the compound is 6-chloro-1,2,3,4-tetrahydroquinazoline-4-spiro-4'-imidazolidine-2,2',5'-trione or a non-toxic pharmaceutically acceptable salt thereof.

6. A method for the treatent of diabetic complications in a warm-blooded animal which comprises administering to said warm-blooded animal an anti-diabetic effective amount of the compound according to claim 1.

7. The method according to claim 6 wherein the compound is 6-chloro-1,2,3,4-tetrahydroquinazoline-4-spiro-4'-imidazolidine-2,2',5'-trione or a non-toxic pharmaceutically acceptable salt thereof.

* * * * *